US009128022B2

(12) United States Patent
Choi et al.

(10) Patent No.: US 9,128,022 B2
(45) Date of Patent: Sep. 8, 2015

(54) MICRO VISCOMETERS AND METHODS OF MANUFACTURING THE SAME

(71) Applicants: Sung Joon Choi, Daegu (KR); Young Taek Cha, Daegu (KR); Dae Young Shin, Incheon (KR); Kang Won Lee, Cheonan (KR)

(72) Inventors: Sung Joon Choi, Daegu (KR); Young Taek Cha, Daegu (KR); Dae Young Shin, Incheon (KR); Kang Won Lee, Cheonan (KR)

(73) Assignee: KOREA INSTITUTE OF INDUSTRIAL TECHNOLOGY, Cheonan (KR)

( * ) Notice: Subject to any disclaimer, the term of this patent is extended or adjusted under 35 U.S.C. 154(b) by 311 days.

(21) Appl. No.: 13/695,619

(22) PCT Filed: Oct. 11, 2012

(86) PCT No.: PCT/KR2012/008227
§ 371 (c)(1),
(2) Date: Nov. 1, 2012

(87) PCT Pub. No.: WO2013/172513
PCT Pub. Date: Nov. 21, 2013

(65) Prior Publication Data
US 2013/0305816 A1    Nov. 21, 2013

(30) Foreign Application Priority Data

May 18, 2012    (KR) .................. 10-2012-0052817

(51) Int. Cl.
*G01N 11/16*    (2006.01)
*G01N 11/10*    (2006.01)

(52) U.S. Cl.
CPC ............... *G01N 11/10* (2013.01); *G01N 11/16* (2013.01)

(58) Field of Classification Search
CPC ..... A61G 7/018; A61G 7/015; A61G 7/0573; A61G 2200/18
USPC .......... 73/54.41, 54.01, 54.24, 64.48, 862.41, 73/862.391, 862.59
See application file for complete search history.

(56) References Cited

U.S. PATENT DOCUMENTS 5,257,529 A    11/1993    Taniguchi et al.
5,825,119 A *  10/1998    Shibata et al. ................ 310/338
(Continued)

FOREIGN PATENT DOCUMENTS

EP    1814170 A3    8/2007
KR    10-0741262 B1    7/2007
KR    2010-0000283 A    1/2010

OTHER PUBLICATIONS

Sungjoon Choi, Wonkyu Moon and Geunbae Lim, "A micro-machined viscosity-variation monitoring device using propagation of acoustic waves in microchannels," Journal of Micromechanics and Microengineering, 20 (2010).

*Primary Examiner* — Hezron E Williams
*Assistant Examiner* — Truong Phan
(74) *Attorney, Agent, or Firm* — Patent Office of Dr. Chung Park (57) ABSTRACT

A viscometer for measuring the viscosity of fluid. The viscometer includes: a first chamber and a second chamber separated from the first chamber; a micro channel connecting the first chamber to the second chamber; a first thin film disposed over the first chamber and a second thin film disposed over the second chamber; and a first piezoelectric film disposed over the first thin film and a second piezoelectric film disposed over the second thin film. At least one of the first and second piezoelectric films has a hexagonal shape if a longest distance between a center and an edge of the piezoelectric film is longer than a threshold range and a circular shape if the distance is shorter than the threshold range.

5 Claims, 11 Drawing Sheets

(56) References Cited

U.S. PATENT DOCUMENTS

| | | |
|---|---|---|
| 6,141,625 A | 10/2000 | Smith et al. |
| 6,322,624 B1 | 11/2001 | Titterington et al. |
| 6,402,703 B1 | 6/2002 | Kensey et al. |
| 6,428,488 B1 | 8/2002 | Kensey et al. |
| 6,571,608 B2 | 6/2003 | Shin et al. |
| 6,624,435 B2 | 9/2003 | Kensey et al. |
| 6,732,573 B2 | 5/2004 | Shin et al. |
| 8,544,316 B2 * | 10/2013 | Choi et al. ............ 73/54.41 |
| 2005/0183496 A1 | 8/2005 | Baek |
| 2007/0246979 A1 * | 10/2007 | Browne et al. .......... 297/216.12 |
| 2008/0134765 A1 | 6/2008 | Baek |
| 2008/0289400 A1 | 11/2008 | Quist |
| 2011/0124124 A1 * | 5/2011 | Shih et al. ............ 436/501 |
| 2012/0189795 A1 * | 7/2012 | Wong .................. 428/36.91 |

* cited by examiner

MICRO VISCOMETERS AND METHODS OF MANUFACTURING THE SAME

CROSS-REFERENCE TO PRIOR APPLICATIONS

This application is a national Stage Patent Application of PCT International Patent Application No. PCT/KR2012/008227, filed on Oct. 11, 2012 under 35 U.S.C. §371, which claims priority of a Korean Patent Application No. 10-2012-0052817, filed on May 18, 2012, which are all hereby incorporated by reference in their entirety.

TECHNICAL FIELD

This present application relates to micro viscometers, and more particularly to micro viscometers with enhanced capability to measure fluid viscosity and methods for manufacturing the same.

BACKGROUND ART

Typically, viscosity is a constant, or a coefficient of fluid and represents the viscous resistance of the fluid. Numerous viscometers have been developed and put into use for the purpose of measuring this coefficient.

In 1953, Greenspan and Wimenitz developed a viscometer to measure the viscosity of a gas, by attaching and facing two Helmholtz resonators towards each other (M. Greenspan and F. N. Wimenitz, "An Acoustic Viscometer for Gases I", NBS Report 2658 (1953)). However, the Greenspan viscometer is relatively large, and displays a 38% margin of error. Thus, the Greenspan viscometer was not considered an ideal solution.

In 1996, K. A. Gillis offered a more precise viscometer than the Greenspan viscometer. A process of experimental error and correction was applied to the design, reducing the margin of error of the viscometer to ±0.5%, which resulted in more accurate gas viscosity (Refer to R. A. Aziz, A. R. Janzen, and M. R. Moldover, Phys. Rev. Lett. 74, 1586 (1995)).

However, in this method, the valid frequency interval is limited to low frequency regions. Gillis' viscometer could only be applied to frequencies under 200 hz. This was due to the fact that the Helmholtz resonator was applied assuming that the product of the wavenumber of the sound wave and the characteristic length was less than 1. In addition, the Gillis viscometer did not take liquid viscosity measurements; only gas viscosity was measured, and the large amount of fluid needed to measure said viscosity made the Gillis viscometer impractical.

In yet another approach, U.S. Pat. No. 6,141,625 discloses a viscosity module with a crystal resonant sensor. It is a portable viscometer capable of measuring viscosity using only a small amount of reagent fluid; viscosity is measured using thin, disc-shaped crystal films.

The resonant frequency of these crystal films is obtained by operating the sensor in thickness shear mode. To do so, a signal is passed through the film, by positioning electrodes on the top and bottom of the crystal film. If a liquid is present on the top portion of the film, the resulting power loss of the signal traveling through an additional barrier will cause damping in the crystal film's resonant frequency. Thus, the viscosity of the liquid is measured by observing the value of damping in the crystal film's resonant frequency.

The issue with the crystal film viscometer, however, is that the viscometer's crystal sensor must be situated horizontally, with a relatively large amount and even distribution of liquid atop the crystal film. This type of viscometer needs several ml of liquid, assuming that the volume of a single water drop is 0.04 ml. It is also impossible to take viscosity measurements with a single drop of liquid. Since this viscometer depends on gravity applied to liquids, measuring gas viscosity is impossible as well.

On the other hand, there are many viscometers which use capillary tubes to measure viscosities. However, most of these viscometers rely on the differential head caused by gravity to take their measurements. Such viscometers are disclosed in U.S. Pat. Nos. 6,322,624, 6,402,703, 6,428,488, 6,571,608, 6,624,435, 6,732,573, 5,257,529, etc. This reliance on the differential head due to gravity means that such viscometers can only measure liquids, not gases. In addition, such viscometers also require large amounts of liquid, ranging from a few dozen to hundreds of ml.

SUMMARY

One embodiment of the present invention provides a viscometer comprising: a first chamber and a second chamber separated from the first chamber; a micro channel connecting the first chamber to the second chamber; a first thin film disposed over the first chamber and a second thin film disposed over the second chamber; and a first piezoelectric film disposed over the first thin film and a second piezoelectric film disposed over the second thin film. At least one of the first and second piezoelectric films has a hexagonal shape if the longest distance between a center and an edge of the piezoelectric film is longer than a threshold range and a circular shape if the distance is shorter than the threshold range.

The micro viscometer may include multiple micro channels.

The threshold distance range is 55 μm-60 μm.

The piezoelectric film has a hexagonal shape or a circular shape when the distance is within the threshold range.

The first and second piezoelectric films may be formed of electroactive polymer.

Another embodiment of the present invention provides a method of forming a micro viscometer, comprising: forming an insulating layer on a silicon-on-insulator wafer; and forming a piezoelectric film by sequentially depositing a lower electrode layer, a piezoelectric layer, and an upper electrode layer on the insulating layer. The planar shape of the piezoelectric film is determined by the longest distance between a center and an edge of the piezoelectric film.

DETAILED DESCRIPTION

The embodiments of the present invention are detailed in the accompanying drawings. The contents of the present invention and accompanying drawings are not limited to the scope of the accompanying drawings, and should be readily apparent to those with ordinary skill in the art.

The present invention includes micro viscometers that have piezoelectric films with optimized shapes to enhance the sensing capability.

Figure 1:
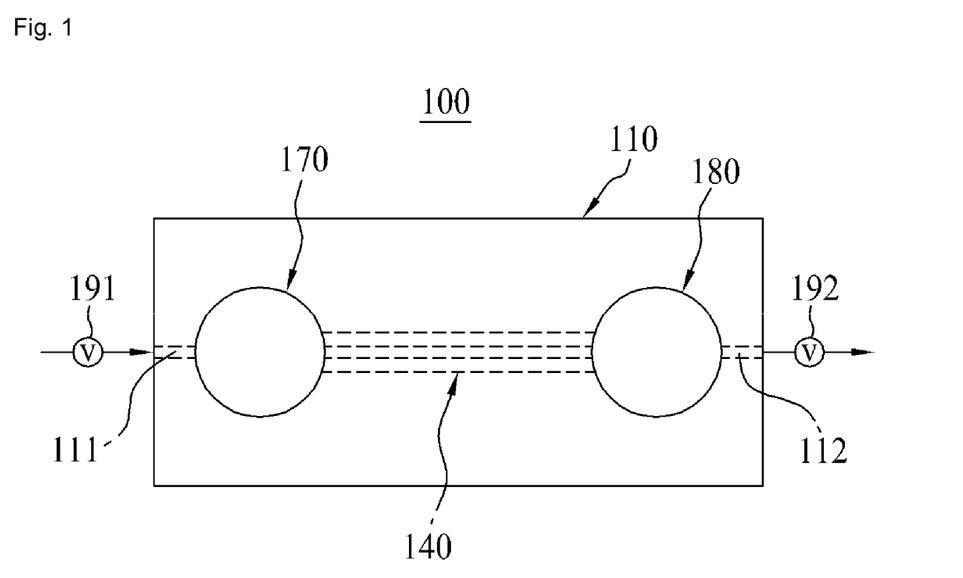
FIG. 1 is a planar view of a micro viscometer in accordance with the first embodiment of the present invention.
Figure 2:
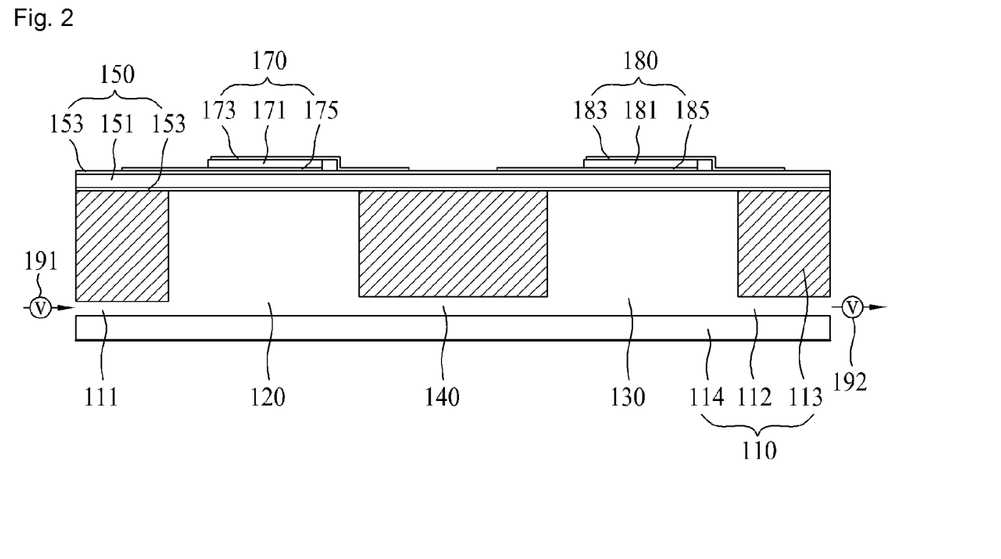
FIG. 2 is a cross-sectional view of a micro viscometer illustrating the first embodiment of the present invention.

FIG. 1 is a planar view of a micro viscometer according to the first embodiment of the present invention, and FIG. 2 is a cross-sectional view of a micro viscometer according to the first embodiment of the present invention.

As illustrated, a micro viscometer 100 positions two Helmholtz resonators in parallel so that viscosity can be measured. The micro-viscometer 100 includes a body 110 having a substrate 113 and a cover 114, a thin film 150, an actuating part 170 and a sensing unit 180.

In body 110, the substrate 113 and the cover 114 are bonded to each other and separated by a preset distance. An inlet 111, an outlet 112, a first chamber 120, a second chamber 130 and a micro channel 140 are formed by dividing a space.

Substrate 113 can be composed of a Silicon On Insulator (SOI) that possesses a silicon single crystal layer on top of the silicon wafer or insulator, and the space for the first chamber 120 and the second chamber 130 can be formed through the Deep Reactive Ion Etching (DRIE) process.

Anodic bonding is performed on the cover 114 and the substrate 113 so that a space including inlet 111, the first chamber 120, the second chamber 130, outlet 112, and micro channel 140 is enclosed. Also, a material of the cover 114 may be transparent material, such as a glass, to confirm a fluid within the cover 114.

On the other hand, the cover 114 may be manufactured from a polymer separately from the substrate and attached. In such a case, the cover may be attached to the substrate by a simple bonding, which reduces the number of required processes. The cover 114 will preferably be made of PMMA (polymethyl methacrylate) or PDMS (polydimethylsiloxane).

At inlet 111 and outlet 112 of main body 110, opening and closing valves 191, 192, are provided respectively, to control the flow of fluid inside the space. The valves may be omitted, depending on the viscosity measurement method.

The first chamber 120, the second chamber 130, inlet 111, and outlet 112 are spatially connected. Preferably, the first chamber 120 and the second chamber 130 have the same volume and height; this minimizes errors in measuring the viscosity of a fluid due to the vibration applied to thin film 150.

A microchannel 140 connects the first chamber 120 and the second chamber 130 together and forms a space where the viscosity loss takes place during viscosity measurement. The micro-channel 140 may include multiple channels. In this case, each micro-channel may have different length, but it should deliver the same acoustic pressure to the sensing unit 180.

Thin film 150 is placed on top of substrate 113 to cover the first chamber 120 and the second chamber 130. Accordingly, the first chamber 120 and the second chamber 130 are separated from the outside by the thin film 150, and, at the same time, vibrates with the fluid filled in the first chamber 120 and the second chamber 130. The thin film 150 includes only one membrane, as shown in FIG. 2, but, in certain embodiments, two separate membranes may be used to cover the first chamber 120 and the second chamber 130, respectively.

In addition, the thin film 150, composed of silicon nitride (SiN), may be deposited on a silicon wafer 151, and may also include two insulating layers 153. In this case, the insulating layer 153 is preferably formed of a Si series insulator, such as silicon dioxide (SiO2).

The actuating part 170 is the first piezoelectric film and is placed over the first chamber 120 to vibrate the thin film 150 so that vibrations will pass through the fluid in the first chamber 120. In this case, for brevity's sake, the thin film 150 corresponding to the first chamber 120 is named as the first thin film.

The actuating part 170 includes the first thin film disposed on the first electrode 175 and the first piezoelectric film 171 disposed over the first electrode 175 and the second electrode 173 disposed over the first piezoelectric film 171. At this point, one side of the second electrode 173 is spaced apart from the first electrode 175 and coupled to the first thin film and the other side of the second electrode 173 is disposed on the surface of the first piezoelectric film 171.

The sensing unit 180 includes a second piezoelectric film and is disposed over the thin film 150 corresponding to the second chamber 130, and senses vibration or pressure of the thin film 150 transferred from the fluid in the second chamber 130. For brevity's sake, a portion of the thin film 150 corresponding to the second chamber 130 is named as second thin film.

The sensing unit 180, like the actuating part 170, includes a third electrode 185 disposed over the second thin film, the second piezoelectric film 181 disposed over the third electrode 185, and a fourth electrode 183 disposed over the second piezoelectric film 181. One side of the fourth electrode 183 is separated from the electrode 185 and coupled to the second electrode, and the other side of the fourth electrode 183 is disposed on a surface of the second piezoelectric film 181.

The actuating part 170 and the sensing unit 180 preferably use piezoelectric materials. In other embodiments, they can be formed of Electroactive Polymer.

To operate the micro viscometer 100, the air inside the body 110 is ejected through the outlet 112. Then, the fluid is filled inside the body through the inlet 111.

At least one of the inner surfaces of the micro viscometer 100 where the fluid directly contacts the micro viscometer 100 is preferably coated with hydrophilic material, where the inner surfaces include inlet 111, outlet 112, first chamber 120, and second chamber 130, and micro channels 140. The coating facilitates the flow of fluid into the body and prevents formation of air pocket caused by surface tension of the fluid.

Then, the shut off valves 191, 192 are closed, thus the fluid within the body 110 is sealed off to prevent flowing from inside the body 110 to the outside. Then, to the pair of the first electrode 175 and the second electrode 173, a sinusoidal voltage (Vinput) having the resonant frequency of the system is applied so that the first piezoelectric film vibrates the first thin film. The Vinput can be expressed by:

$$V\text{input} = V_0 \sin \omega t \qquad \text{Equation 1:}$$

When the first thin film vibrates, an acoustic boundary layer formed inside the body 110 causes a loss of acoustic vibrations. Such loss includes two parts: the loss in the viscous boundary layer ($\delta v$) formed in the micro channel 140 where the particle speed is the fastest, and the thermal loss in the thermal layer ($\delta t$) formed in the first chamber 120 and the second chamber 130 where the surface-to-volume is large.

If the viscous boundary layer or thermal boundary layer is much smaller than the radius or ½ of the height (rc), the Q factor of these losses can be expressed as:

$$\frac{1}{Q} = \frac{\alpha_v}{2\pi} + \frac{\alpha_t}{2\pi} = \frac{\delta_v}{r_c} + (\gamma - 1)\frac{\delta_t S}{\pi V} \qquad \text{Equation 2}$$

Here, r is ratio of specific heat, s is the chamber surface area, and v is the volume of the chamber, $\delta v$ is the viscous boundary layer thickness inside micro-channel 140, and $\delta t$ indicates the thickness of the thermal boundary layer in chambers 120,130.

Acoustic losses in sound waves are passed to the second thin film, and the sensing unit 180 can measure the frequency response of the second thin film. Upon measuring the frequency response and calculating Q factor by equation 2, the viscosity of the fluid can be determined by:

$$v = \frac{\mu}{\rho} = \frac{\omega r_c^2}{2}\left\{\frac{1}{Q} + (1-\gamma)\frac{\delta_t S}{\pi V}\right\}^2 \qquad \text{Equation (3)}$$

Here, v is the dynamic viscosity coefficient, μ is the viscosity coefficient, and ρ is density.

Alternatively, according to the present invention, micro-viscometer 100 may measure the viscosity using single frequency (or, resonant frequency); the measurement method is named as Single-Frequency Driving Method (SFDM). This alternative method is described below.

The method described above, which is based on the Q factor, requires sweeping a frequency interval to find out both the resonant frequency and half power band width. This error in finding the resonant frequency and the half power bandwidth may cause some error in calculating the Q factor. The SFDM does not determine the Q factor; instead, only the resonant frequency is used to measure the viscosity and its variation.

Figure 3:
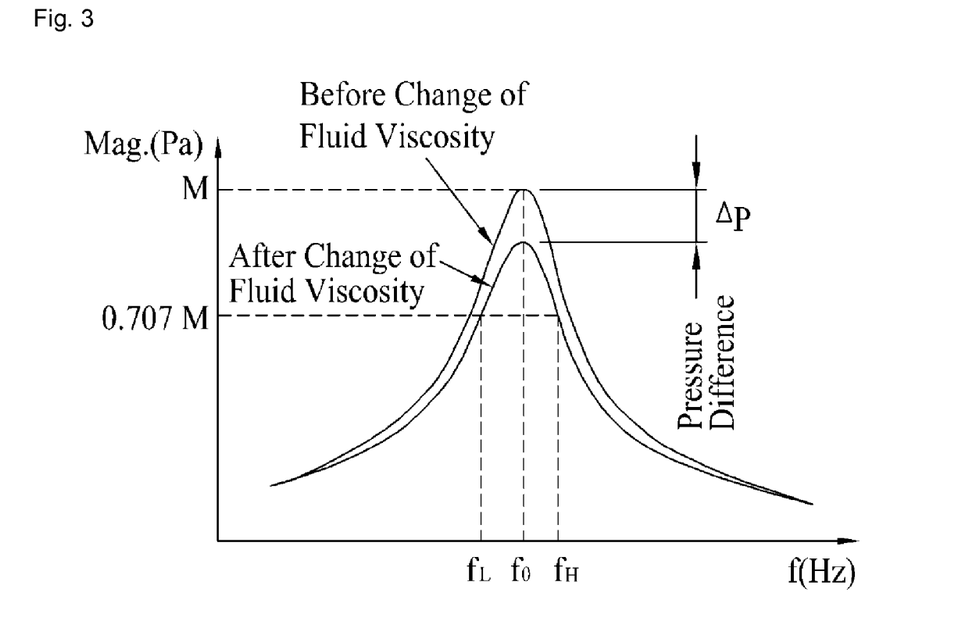
FIG. 3 is a graph illustrating the method of measuring the viscosity using a resonant frequency from a micro viscometer, according to one embodiment of the present invention.

As shown in FIG. 3, the viscosity of the fluid changes the acoustic pressure or phase difference (Δp) at the resonant frequency. At that point, by measuring the variation of these quantities, the change in viscosity of the fluid can be detected and through the calibration process, thus the change in viscosity can be measured.

Figure 4:
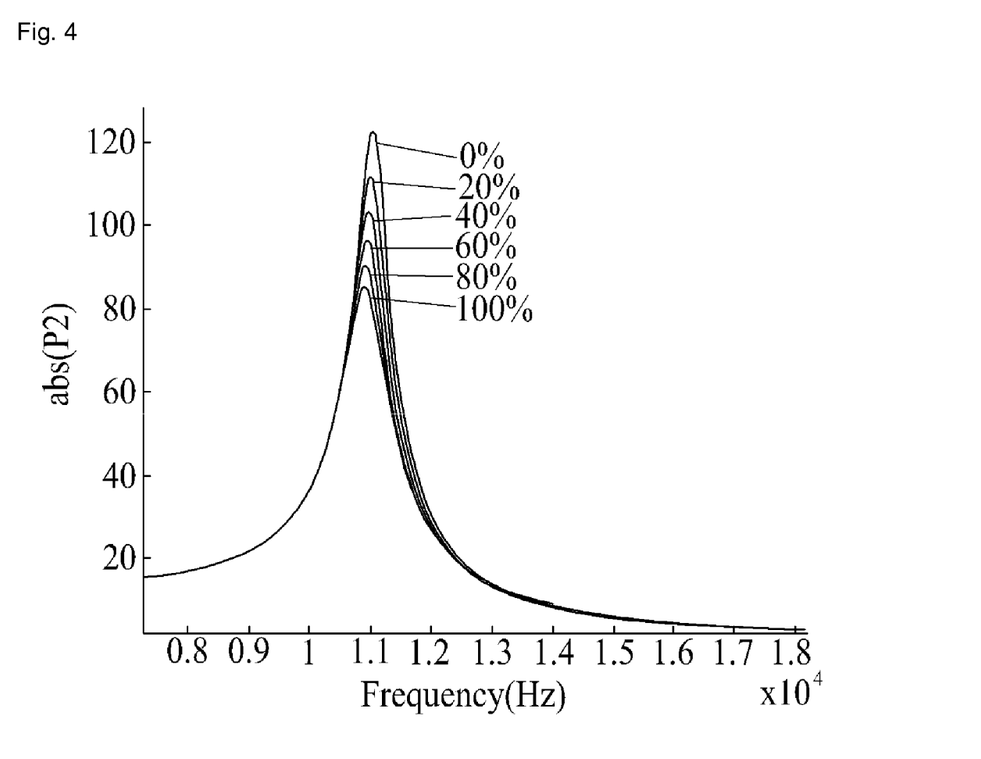
FIG. 4 is a graph illustrating the method of measuring the viscosity of the fluid using resonant frequency from a micro viscometer, according to one embodiment of the present invention.

The sensing unit 180 measures the pressure as the frequency of the actuating part 170 is changed, and also, as the viscosity of standard fluid, such as water, is increased. As shown in FIG. 4, the viscosity is changed by a preset interval: 20%, 40%, 60%, 80% and 100%, for example. For each viscosity, the pressure measurement according to the frequency variation is obtained and stored in a database.

Then, the sensing unit 180 measures the pressure change of the query fluid as the actuating part 170 applies varying frequencies. Next, by searching the database to find a pressure change that coincides with the obtained pressure change, the viscosity can be determined. The viscosity interval is not limited to 20%; the measurement of the pressure change in the standard fluid may be performed at any suitable viscosity interval.

In addition, as shown in FIG. 3, the frequencies, fL and fH, corresponding to $1/\sqrt{2}$ of the peak pressure point can be measured either before or after the viscosity is changed. Then, the Q factor can be obtained by equation 4 and the viscosity can be calculated by equations 2 and 3.

$$Q = \frac{f_o}{f_H - f_L} \qquad \text{Equation (4)}$$

A Helmholtz resonator is used when the system size is much smaller than the frequency wavelength (kl<<1), where k is the wavenumber and l is the length of the micro channel 140, and the frequency of wave typically ranges from tens to hundreds Hz.

In contrast, in some embodiments, the micro viscometer may be fabricated by a MEMS process and thus, is much thinner and smaller than the conventional viscometer. As such, the resonant frequency of the system may arise up to thousands, or hundreds of thousands Hz.

It may be possible that the present system may not be able to meet the Helmholtz resonance requirement, kl<<1, which may require interpretation of the data. In embodiments, the total acoustic impedance of the system can be calculated by equation 5, and the resonant frequency can be found when the reactance term becomes zero, as shown in equation 6:

$$Z_{ac} = Z_{mem1} + Z_{ca1} + 2Z_{ac} + Z_{mc} + Z_{ca2} + Z_{mem2} \qquad \text{Equation 5}$$

In this case, the impedance for each is listed below.

$$Z_{mem1} = \frac{K_{ac}^{mem1}}{j\omega}$$

represents the acoustic impedance of the first film 150, and $$Z_{mem1} = \frac{K_{ac}^{mem2}}{j\omega}$$

represents the acoustic impedance of the second thin film 160, and $$Z_{ca1} = \frac{Z_o}{j\tan kh_1}\frac{1}{S_1}$$

represents the acoustic impedance of the first chamber 120, and $$Z_{ca2} = \frac{Z_o}{j\tan kh_2}\frac{1}{S_2}$$

represents the acoustic impedance of the second chamber 130, and $$Z_{mc} = j\frac{Z_o \tan kl}{A}$$

represents the acoustic impedance of the micro channel 140, and $$Z_{end} = \frac{Z_o}{A}\{R_1(2kr_c) + jX_1(2kr_c)\}$$

represents the impedance of the Inlet 111 and outlet 112.

In addition, $K_{ac}^{mem1}$ and $K_{ac}^{mem2}$ represent the acoustic stiffness of the first and second films, respectively, and h1 and h2 represents the heights of the first chamber 120 and the second chamber 130. In the equation above for Zend, $$R_1(2kr_c) = 1 - \frac{2J_1(2kr_c)}{2kr_c}$$

(J1 is the Bessel function), $$X_1(2kr_c) = \frac{2H_1(2kr_c)}{2kr_c}$$

(H1 is the first orer struve function.)

Assuming the first chamber 120 and the second chamber 130 have the same size and shape, Zac can be further simplified, and then, to find the resonant frequency, the reactance term of Zac can be expressed as equation 6:

$$\text{Im}(Z_{ac}) = \frac{2Z_0}{A}\left\{\frac{2}{2kr_c}\left[\frac{2}{\pi} - J_0(2kr_c) + \left(\frac{16}{\pi} - 5\right)\frac{\sin(2kr_c)}{2kr_c} + \left(12 - \frac{36}{\pi}\right)\frac{1-\cos(2kr_c)}{(2kr_c)}\right] + \frac{\tan kl}{2}\right\} - \left\{\frac{2Z_0}{\tan kh}\frac{1}{S} + \frac{2K_{ac}^{mem}}{\omega}\right\}$$

Equation 6

Therefore, the equation $\text{Im}(Z_{ac})=0$ can be solved to find the k that corresponds to the resonant frequency. If the value of k is expressed as x, x is expressed by equation 7:

$$K_n = X_x (n\text{:interger})$$

Equation 7:

Resonant frequency can be obtained as shown in Equation 8 below.

$$f_1 = \frac{k_1 c_0}{2\pi} = \frac{x_1 c_0}{2\pi}$$

Equation 8

Figure 5:
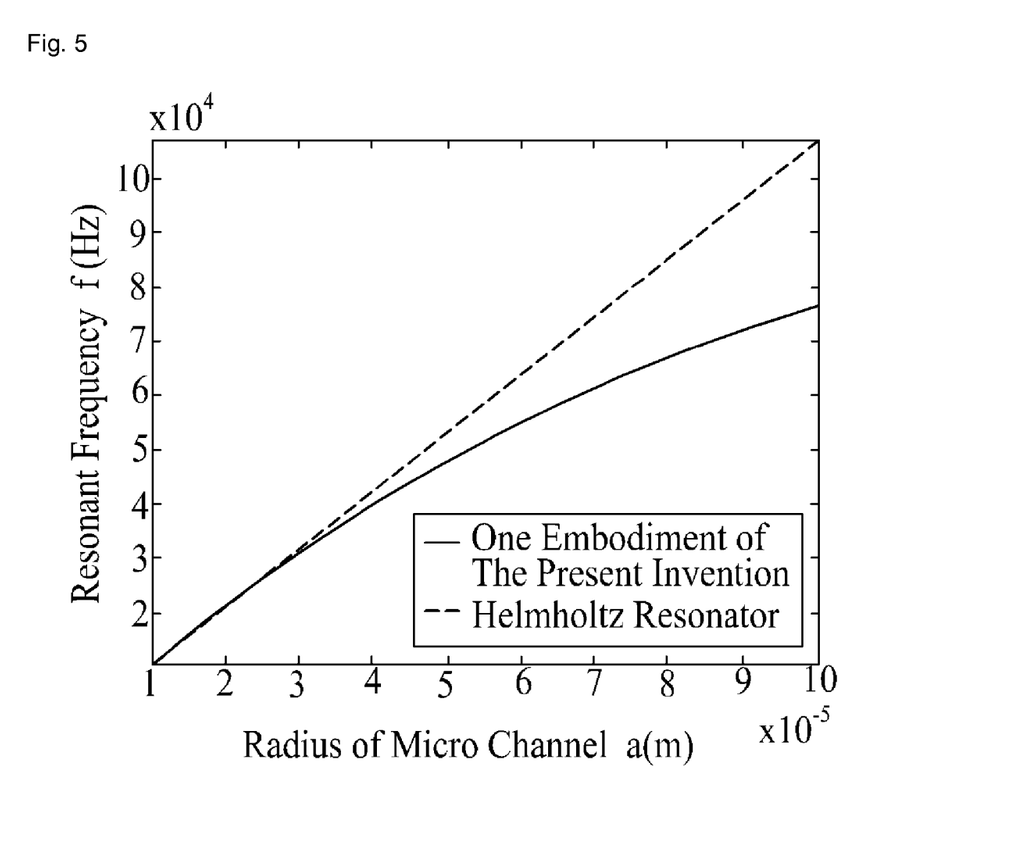
FIG. 5 is a graph comparing the difference of results between the calculation method of the Helmholtz resonator when kl<<1 and the calculation method according to one embodiment of the present invention disregarding the value of kl.

FIG. 5 shows comparison between a case where the Helmholtz resonance condition, kl<<1, is satisfied and a case where the present method of the embodiments is applied without being limited by the Helmholtz resonance condition. As shown, the resonant frequency of the present method approaches to that of the Helmholtz resonance method when the radius ra of the micro channel 140 and the wavenumber are low (kl<<1). However, the Helmholtz resonance method cannot be applied when ra increases to fail the condition, kl<<1, and, in such cases, the present method should be used to calculate the resonant frequency.

Figure 6:
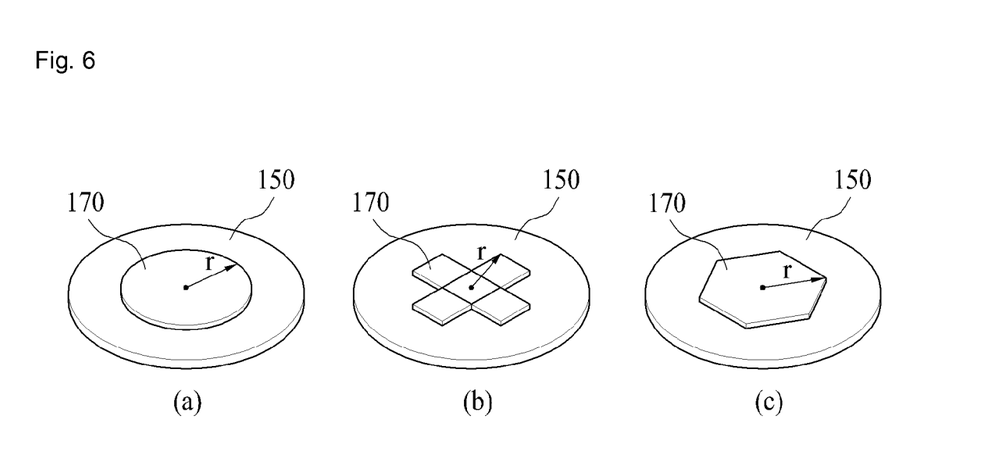
FIG. 6 is an illustration of the piezoelectric film shapes of a micro viscometer according to one embodiment of the present invention.
Figure 7:
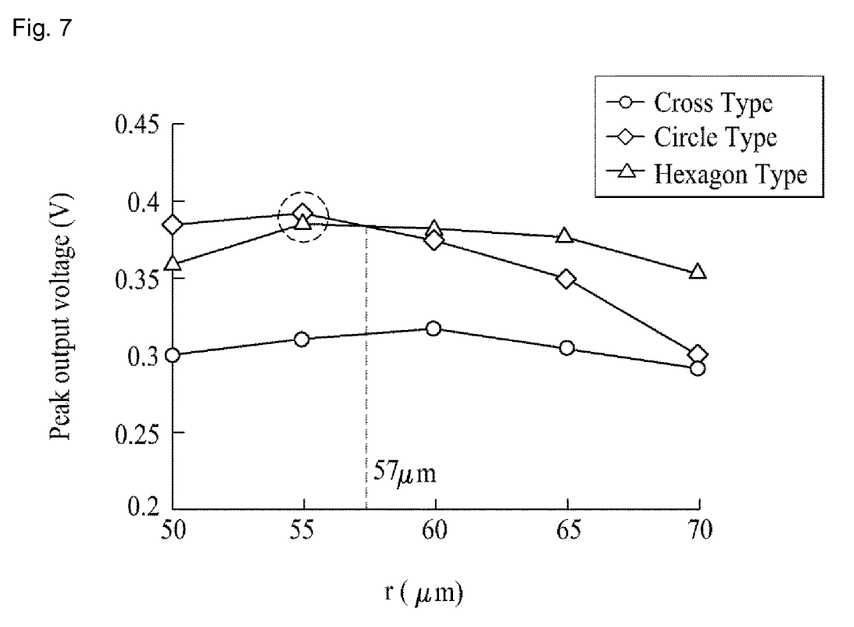
FIG. 7 is a graph illustrating the changes in peak output voltages of the sensing portion depending on the shape of the piezoelectric film and the distance from the center of the piezoelectric film to its edge.

FIG. 6 illustrates the planar shapes of piezoelectric films (or, equivalently, piezoelectric film) of a micro-viscometer according to the present invention. FIG. 7 shows the peak output voltage measured by the sensing unit as functions of the shapes in FIG. 6 and the distance (r) between the center and edge of each piezoelectric film.

First, FIG. 6(*a*) shows a circle type piezoelectric film 170 disposed on the Si film 150, FIG. 6(*b*) shows a cross type piezoelectric film 170 disposed on Si film 150, and FIG. 6(*c*) shows a hexagon type piezoelectric film 170 disposed on the Si film 150.

Of each shape, the radius of the piezoelectric film (r) is measured from the center of the piezoelectric film to the edge of the piezoelectric film. The magnitude of the radius (r) is within a threshold limit for having sensing capabilities and can range between 50 μm to 70 μm.

FIG. 7 shows the peak output voltage measured by the sensing unit as functions of the shapes in FIG. 6 and the distance (r) between the center and edge of each piezoelectric film. Table 12 shows exemplary sizes of various elements in FIG. 6, where the thicknesses of circle type, cross type, hexagon type, the widths/radii and thickness of Si thin film, and the widths/radii and heights of the chambers covered by Si thin film are the same.

TABLE 1

| Types | Radius or width * length, μm | Height, μm |
|---|---|---|
| Si thin film (circle type) | 90 | 10 |
| Chamber (circle type) | 90 | 430 |
| Piezoelectric film (circle type) | R (50-70) | 3 |
| Micro channel (rectangle type) | 30 * 2160 | 30 |

The higher the peak output voltage, the better performance of the piezoelectric film. As shown in FIG. 7, the peak output voltage varies depending on the shape of the piezoelectric film when the radius is fixed to 57 μm. When the radius is larger than 57 μm, the hexagon type gives the highest output voltage. When the radius is smaller than 57 μm, the circle type gives the highest output voltage.

The output voltage varies depending on the shape of the piezoelectric film when the radius is 57 μm. However, when the radius is within the range of 55 μm-60 μm, the difference between output voltages from the hexagon type and the circle type is not large, and thus, the piezoelectric films of circle and hexagon types have the enhanced piezoelectric performance when the radius ranges 55 μm-60 μm (threshold range).

When the radius is within the threshold range, the performance of the piezoelectric film changes depending on its shape. Also, the threshold range can change if the other conditions, such as the radii of Si thin film and chamber, the length and width of the micro channel, change.

For example, the threshold range may increase or decrease in proportion to the size or width of the Si thin film, and the thickness of Si thin film or piezoelectric film may increase or decrease in proportion under the same condition.

Figure 8:
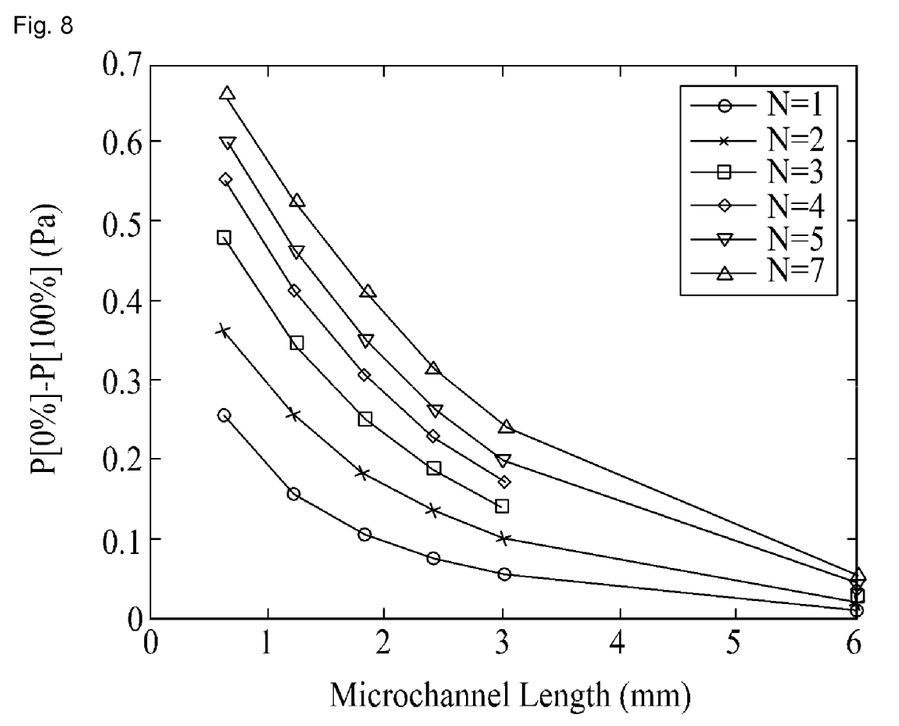
FIG. 8 is a graph of the difference in acoustic pressure according to the number of micro channels and fluid viscosity, according to one embodiment of the present invention.
Figure 9:
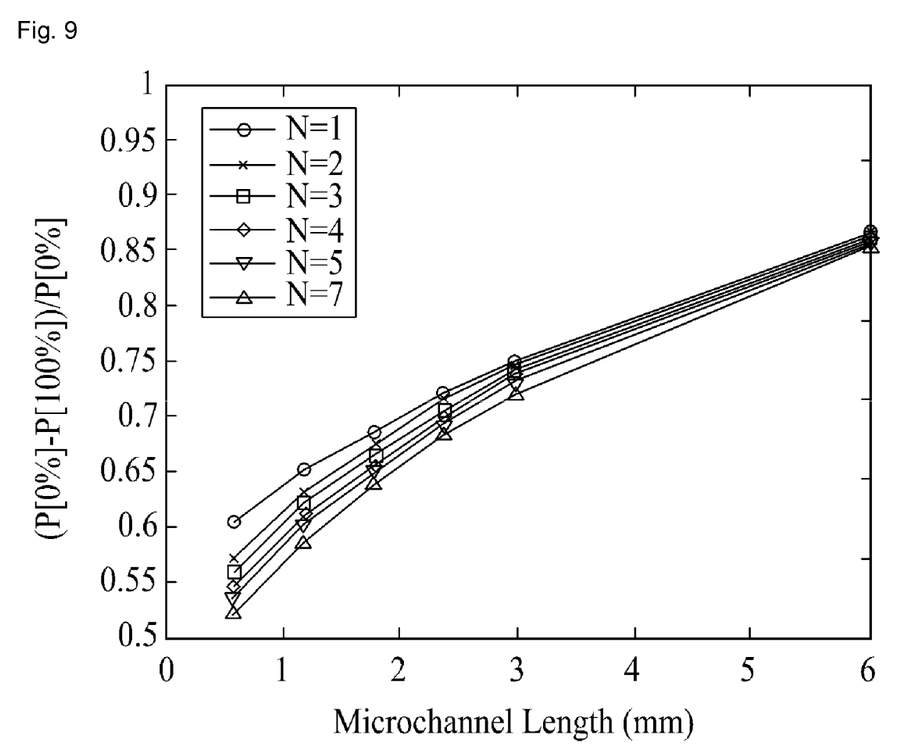
FIG. 9 illustrates the rate of change in acoustic pressure according to the number of micro channels along with FIG. 8, according to one embodiment of the present invention.

FIG. 8 shows the absolute difference in acoustic pressure as a function of micro channel length at various numbers of channels. FIG. 9 shows the relative difference in acoustic pressure under the same condition as FIG. 8.

As depicted in FIGS. 8 and 9, a micro viscometer having multiple channels shows a smaller variation in relative pressure than a viscometer having one channel, but shows a larger variation in absolute pressure.

For example, in FIG. 8, when the length of a micro channel is 3 mm, the absolute pressure changes are 0.05 Pa and 0.25 Pa when the numbers of channel are 1 and 7, respectively. But, in FIG. 9, the relative pressure change is 0.75 and 0.72, respectively.

In other words, the intensity of delivered acoustic pressure increases as the number of micro channel increases, and the sensing unit has an improved signal-to-noise ratio during operation.

Figure 10:
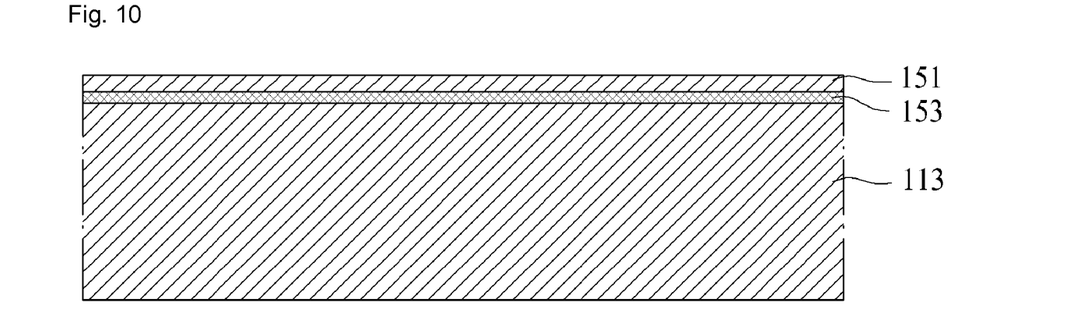
FIG. 10-15 is an illustration of how a micro-viscometer may be fabricated according to one embodiment of the present invention.

FIGS. 10-15 illustrate how to fabricate a micro viscometer according to the present invention. In FIG. 10, a Silicon on insulator (SOI) wafer having SiO2 layers is prepared.

Figure 11:
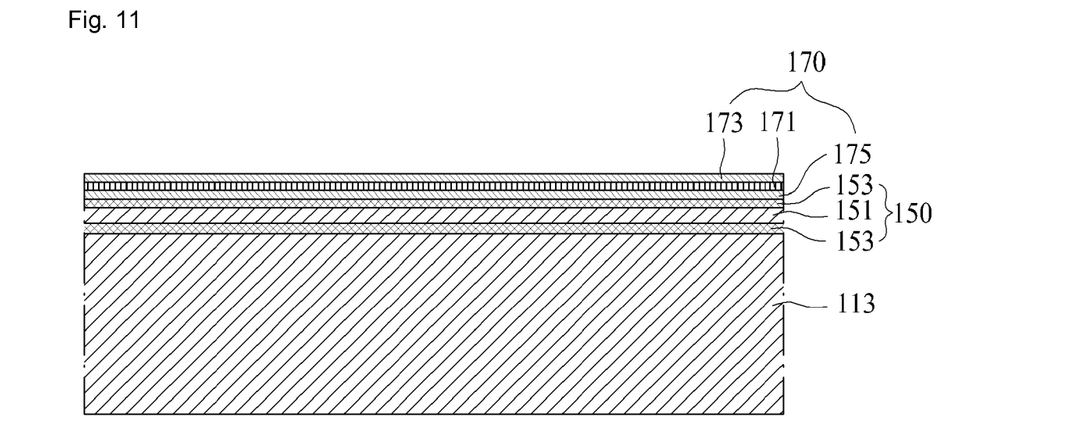

Then, as shown in FIG. 11, an insulating layer 153 is formed on the SOI wafer by heat to thereby form a thin film 150 having two insulating layers 153 over and under the silicon 151. Then, the lower electrode layer 175, piezoelectric layer 171, and upper electrode layer 173 are deposited to form piezoelectric film 170.

Figure 12:
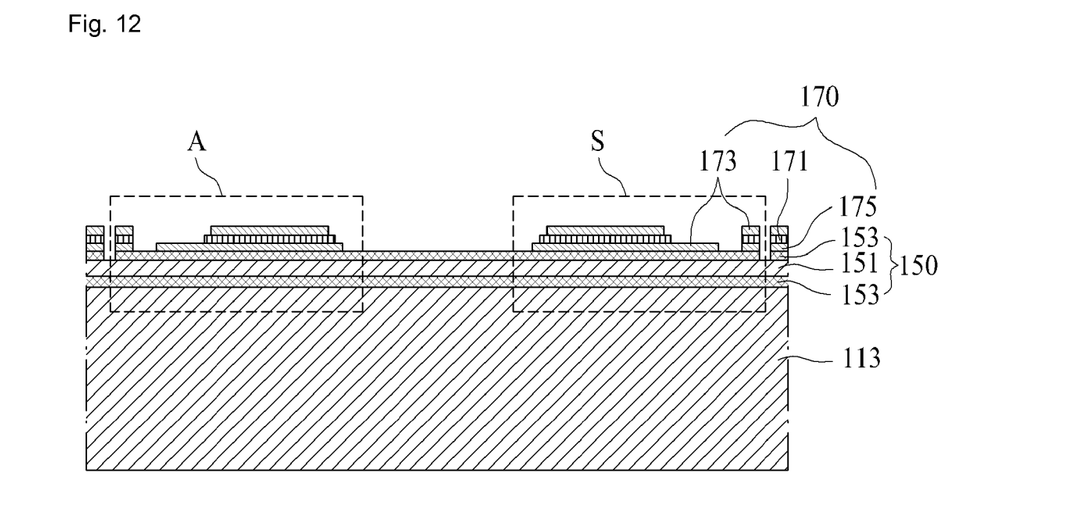

Then, as shown in FIG. 12, the lower electrode layer 175, piezoelectric layer 171, and upper electrode layer 173 are patterned to produce the intended shape. The piezoelectric film 170 is separated into the first and second parts (A and B) to form actuating part and sensing unit, respectively.

The piezoelectric film 170 is patterned to have a specific shape, where the shape is selected based on the longest distance from the center to an edge of the piezoelectric film 170.

The piezoelectric film 170 has a hexagonal shape if the distance is longer than the threshold range, and a circular shape if the distance is shorter than the threshold range, where the threshold range is 55 µm-60 µm.

The patterning method may be, but not limited to, screen printing, areo-sol, chemical vapor deposition, or sputtering, for instance.

Figure 13:
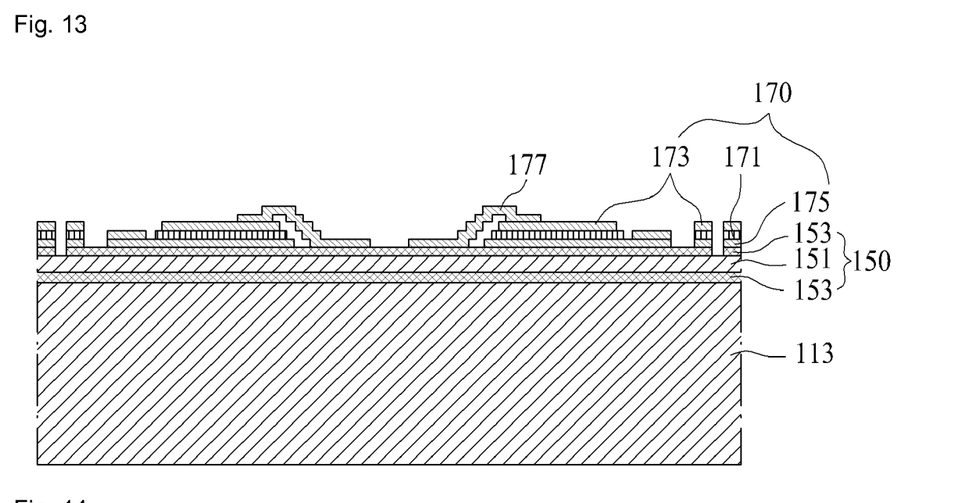

Then, to form a bridge electrode 177, a photoresistor is spin-coated and patterned on the patterned upper electrode layer 171, and a gold layer (Au) is deposited on the upper electrode 171 to cover the photoresistor. Then, a photoresistor is spin-coated on the gold layer, patterned to have an electrode shape, and etching the gold layer. Finally, the photoresistor is removed by etching to a bridge electrode.

Figure 14:
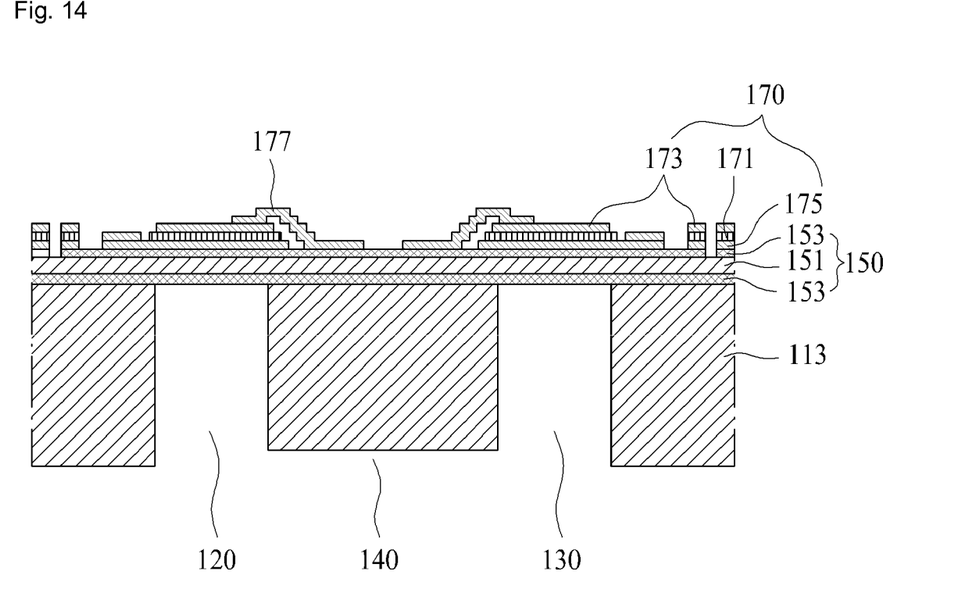

Next, as shown in FIG. 14, a micro channel 140 is formed on a portion of the SOI wafer surface where the insulating layer is not formed. Also, chambers 120 and 130 corresponding to the first and second parts, respectively, are formed. The micro channel 140 and the chambers 120, 130 may be formed by Deep-Reactive-Ion-Etching method.

Figure 15:
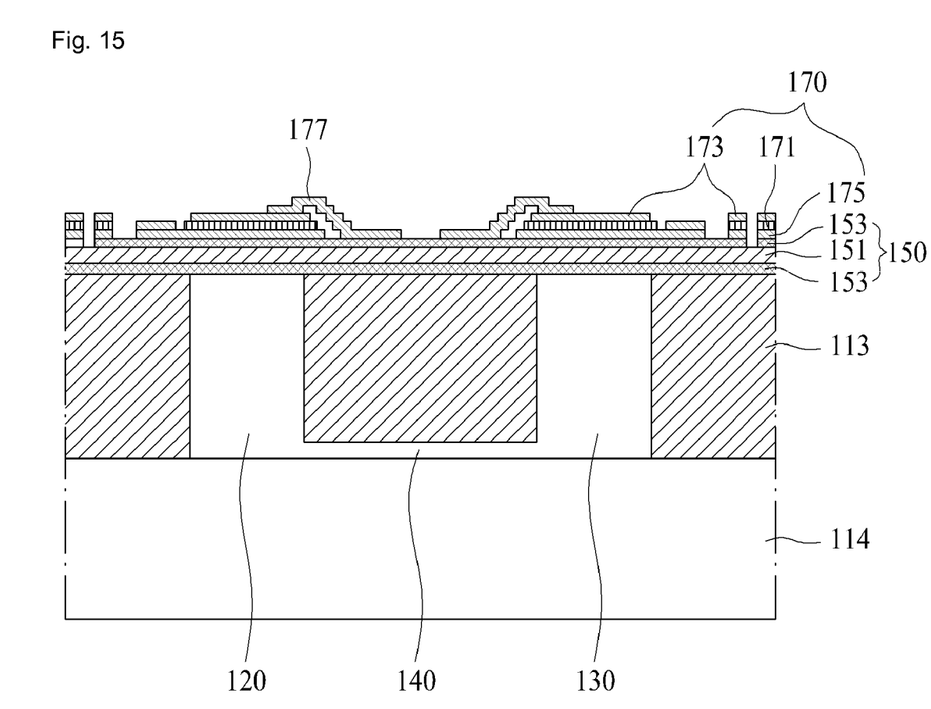

Finally, as shown in FIG. 15, a cover 114 made of transparent material is attached to the surface of SOI so that the micro channel and chambers are divided in space. The cover 114 may be made of PMMA or PDMS, while other suitable materials may be used to make the cover.

The micro viscometer of the present invention has a piezoelectric film possessing enhanced performance that enables accurate measurement of fluid viscosity. It also can measure the viscosity of a gas as well as a fluid, and the size is smaller than any existing viscometer. It can be used as an independent device to measure only viscosity, or, it may form a part of other device while it still measures viscosity.

In addition, the micro viscometer of the present invention may be applied to measurements of blood viscosity, Micro PC-Al (Micro PCR) amplified DNA viscosity, and other various biological liquid material viscosity.

The persons having ordinary skills in the art will understand that various altered or modified examples can be made through the matters described above without departing from the technical concept of the present invention. The scope of the present invention does not reside in the above description, rather in the following claims, and all differences within equivalents thereof should be intended to be included in the present invention.

What is claimed is:

1. A micro viscometer, comprising:
   a first chamber and a second chamber separated from the first chamber;
   a micro channel connecting the first chamber to the second chamber;
   a first thin film disposed over the first chamber and a second thin film disposed over the second chamber; and
   a first piezoelectric film disposed over the first thin film and a second piezoelectric film disposed over the second thin film,
   wherein the first and second piezoelectric films have a hexagonal shape if a longest distance between a center and an edge of at least one piezoelectric film is longer than a threshold range and the first and second piezoelectric films have a circular shape if the distance is shorter than the threshold range,
   wherein the threshold range is 55 µm-60 µm.

2. The micro viscometer of claim 1, wherein the viscometer includes a plurality of the micro-channels.

3. The micro viscometer of claim 1, wherein the first and second piezoelectric films have a hexagonal shape or a circular shape when the distance is within the threshold range.

4. The micro viscometer of claim 1, wherein the first and second piezoelectric films are formed of an electroactive polymer.

5. The micro viscometer of claim 1, wherein the threshold range increases or decreases in proportion to a width or thickness of at least one of the piezoelectric films.

* * * * *